United States Patent [19]

Clarke, Sr. et al.

[11] Patent Number: 5,689,241

[45] Date of Patent: Nov. 18, 1997

[54] SLEEP DETECTION AND DRIVER ALERT APPARATUS

[76] Inventors: James Russell Clarke, Sr.; Phyllis Maurer Clarke, both of 184 Homestead Pl., Bridgeton, N.J. 08302

[21] Appl. No.: 656,053

[22] Filed: May 31, 1996

Related U.S. Application Data

[63] Continuation-in-part of Ser. No. 432,419, Apr. 24, 1995, abandoned.

[51] Int. Cl.$^6$ ........................................... G08B 21/00
[52] U.S. Cl. ............................. 340/575; 340/576
[58] Field of Search ............................. 340/575, 576

[56] References Cited

U.S. PATENT DOCUMENTS 4,854,329  8/1989  Walruff ................................ 340/576
5,353,013  10/1994  Estrada ............................... 340/575

*Primary Examiner*—Glen Swann
*Attorney, Agent, or Firm*—John D. Gugliotta

[57] ABSTRACT

A sleep detection and driver alert apparatus has a compact housing that can be placed around the rearview mirror or on the dashboard. It contains all lenses and electronic detection mechanisms for monitoring the effects of early impending sleep by means of an infrared auto-focusing, digital, image stabilizing lens with zoom capability. Additionally, the unit contains an added infrared thermal sensor for the monitoring and evaluation of different ambient temperatures around the facial areas of the nose and mouth. These temperature changes will be that of the exhaled gas plume of normal breathing patterns, which will lower in volume as the driver begins to hypoventilate, thus increasing their blood level of carbon dioxide which is in most part the reason for early drowsiness associated with sleep. The device will monitor via the infrared camera the thermal image changes in pixel color of open versus closed eyes of the driver via the temperature sensitive infrared portion of the digitized photographic image passed through a video charge coupling device. The combination of non movement and a decrease in breath temperature, which is a physiological response to hypoventilation thus initiating drowsiness, will trigger the infrared camera to zoom onto the eye region of the driver. This combined data is routed to the sleep status microprocessor memory via the optical image detector and thermal sensor for data changes above or below baseline data measurements.

11 Claims, 5 Drawing Sheets

SLEEP DETECTION AND DRIVER ALERT APPARATUS

RELATED APPLICATIONS AND DISCLOSURE DOCUMENTS

This application is a continuation in part of the invention described in application Ser. No. 08/432,419, filed Apr. 24, 1995, and now abandoned.

BACKGROUND OF THE INVENTION

1. Field of the Invention

The present invention relates generally to sleep detection devices, and, more particularly, to an apparatus to detect the early stages of sleep in a driver of a motor vehicle which provides an alarm means for warning and/or waking the driver.

2. Description of the Related Art

As is well-known in the art, a number of different physical phenomena can be monitored and measured in order to detect the onset of sleep in the driver of a vehicle. Simple devices, such as foot switches which must be kept activated by a driver's foot, or electrical contacts attached to the eyelids of drivers to detect closing of the driver's eyes have proved to be ineffective due to one or more major shortcomings. Primarily, those devices which required direct physical contact with the driver tend to be awkward, uncomfortable, or inconvenient, and thereby end up ineffective due to their disuse in practice.

Another problem occurs from devices that attempt to detect driver sleepiness by monitoring indirect evidence of sleep. Particularly, by monitoring of the position of the steering wheel, by measuring the driver's grip on the steering wheel, by counting blinks, or merely by attempting to measure the position of the driver's eyelids have all been used unsuccessfully to detect sleepiness in a driver of a motor vehicle.

Numerous attempts have been made to correct the foregoing problems. For instance, U.S. Pat. No. 3,631,446, issued in the name of Setner, discloses a sleep-sensing device for use on automobile vehicles. However, a sleep-sensing device for use on automobile vehicles made in accordance with this reference is associated with several drawbacks. For example, the Setner reference discloses a method of detecting sleep in a driver by monitoring normal movement of the vehicle's steering wheel. However, this reference is prone to false alarms in that it does not allow for long, straight, smooth sections of highway. These are the very situations that are likely to contribute to drowsiness in a driver. Moreover, such a device is not readily adaptable to other vehicle operations, such as airplanes, where vehicle speed or wheel movement patterns are completely different than those for an automobile.

Additionally, U.S. Pat. No. 3,678,494 also issued in the name of Setner discloses a sleep sensing apparatus for use on automotive vehicles. This second Satner reference discloses a programmable device that also monitors the vehicle's steering wheel activity, but allows for variances that result at different vehicle speeds.

In U.S. Pat. No. 4,210,905 issued in the name of Coons, an alarm for waking a dozing driver is disclosed. The Coons reference discloses a plurality of electrical switches arranged about a steering wheel of a vehicle which require the driver to maintain a constant firm grasp on the wheel to prevent an alarm from sounding. The Coons reference increases effort and fatigue on the driver and fails to accommodate toll gates, parking lots, or other situations where the driver may want or need to remove both hands from the wheel, at least momentarily.

In U.S. Pat. No. 4,564,833 issued in the name of Seko et al., a dozing warning system for a vehicle is disclosed. In the Seko et al. reference, a device is disclosed which provides pulses indicative of the steering angle and steering direction, and monitors such pulses for comparison in order to determine that a driver is sleeping. Once again, the Seko et al. reference relies on indirect evidence of sleep, i.e. it monitors operation of the vehicle and not the driver.

In U.S. Pat. No. 4,875,030 issued in the name of Chiu, a sleep preventing alarm device is disclosed. In the Chiu reference, the preferred embodiment is contained in a device that resembles a pair of reading glasses which is then worn by the user. In the Chiu reference, the position of the wearer's eyelids are monitored, and a buzzer is sounded in the wearer's ear if the eyelids remain closed past a predetermined period of time. However, a major problem with the Chiu reference is that it must, at the very least, be worn by the user in order to be effective.

Finally, in U.S. Pat. No. 4,953,111 issued in the name of Yamamoto et al., a doze detector is disclosed which reference the use of two reflection type sensors to detect blinks of the user's eyes. As with Yamamoto et al and other references, blinking is the only measure of sleepiness which is utilized, and the sensors must remain in close proximity to the user.

Consequently, a need has been felt for providing an apparatus and method which overcomes the problems associated with monitoring vehicular functioning rather than direct evidence of sleep itself. Additionally, a need has been felt to provide such an apparatus and method which overcomes the problems associated with direct contact or user warn devices.

SUMMARY OF THE INVENTION

It is therefore an object of the present invention to provide an improved sleep detection and driver alert apparatus.

It is a further object of the present invention to provide an improved sleep detection and driver alert apparatus that may be suited to be attached to the rear view mirror or upon the vehicle dash board.

It is a further object of the present invention to provide an improved sleep detection and driver alert apparatus that utilizes digital infrared auto-focus image stabilization zoom camera lens technology to maintain a physically remote monitoring of a user's eye-nose area, thereby eliminating the need for a user worn or a close proximity device.

It is a further object of the present invention to provide an improved sleep detection and driver alert apparatus that measures and determines changes in heat output between open eyes and closed eyes via pixel color change with infrared imaging.

It is a further object of the present invention to provide an improved sleep detection and driver alert apparatus that measures and determines changes in heat output from changes in respiration via an infrared thermal sensor.

It is a further object of the present invention to provide an improved sleep detection and driver alert apparatus that can provide an escalating series of audible alarms in order to awaken or alert a sleepy driver.

It is a further object of the present invention to provide an improved sleep detection and driver alert apparatus that is self calibrating to assure proper operation with users of different size, height, and other physical characteristic.

It is a feature of the present invention to provide an improved sleep detection and driver alert apparatus that utilizes both auto focusing image as well as sensing heat variation of the closed eyes via pixel color changes with infrared imaging and temperature changes in exhaled breathing as an indicator of the onset of sleep or drowsiness.

Briefly described according to one embodiment of the present invention, a sleep detection and driver alert apparatus is provided that consists of a compact housing that contains all lenses and electronic devices such that it may fit around a rear view mirror or on a dashboard. The housing contains an image stabilization digital infrared auto-focus camera lens calibrated to a short distance of one to three feet to monitor the eye-nose area. An infrared thermal sensor detects heat loss/gain change in ambient facial temperature from exhaled breath. An alarm provides multiple levels of warning, varying in degree based upon the frequency and duration of detected sleep episodes.

An advantage of the present invention is that it is based upon primary characteristics of sleep itself and not on secondary characteristics such as vehicle operations. Generally, the present invention utilizes the understanding that most early sleep does not come suddenly, but in stages of disorientation from a trance-like state to a slow blinking eyelid closure. By utilizing digital infrared imaging the present invention can detect the heat variations that occur from the increased capillary blood flow in closed eyes by changes in the color pixel count.

Another advantage of the present invention that utilizes the understanding of the stages of early sleep allows the present invention to be mounted remotely, either on the rear-view mirror on in the dashboard. Invariably the head of the driver takes on a fixed posture during the early stages of sleepiness, with minimal head movement. Next, a fixed gaze results until a slow eyelid closure occurs. At this stage of drowsiness one becomes less alert and disoriented, and is most likely to lose control of a vehicle. The present invention will be continuously auto focusing on the face/eye area to obtain an accurate image of the drivers head and eye movement. The present invention utilizes the non-movement of the head and detecting of eyelid closure as a first stage detection of sleep. Only if head movement decreases and the eyelids are sensed closing 60% is the heat output infrared pixel color measured to indicate sleep.

Further, another advantage of the present invention that results from monitoring several different characteristics of sleep is the reduction in the number of false alarms that can result from hand movement, sun glare, head movements, and the like.

BRIEF DESCRIPTION OF THE INVENTION

A sleep detection and driver alert system is presented that consists of alarms for warning a vehicle driver that he or she is falling asleep while driving. The unit consists of a compact housing that contains all lenses and electronic detection devices for monitoring the effects of impending sleep via a digital infrared thermal sensor and an infrared auto-focusing image stabilization lens with added zoom capabilities. The device can be placed on the dashboard or around the rearview mirror.

The autofocus electronics of the camera will be utilized to monitor head movements while an infrared thermal sensor analyzes exhaled breath temperatures. The combination of non-movement and a decrease in ambient breath temperature, which is a physiological response to the onset of sleep, will trigger the infrared camera to zoom onto the eye region of the driver. The infrared camera will then analyze thermal image changes in pixel color of open versus closed eyes of a driver via the temperature sensitive infrared image portion of digitized photographic images passed through a video charge couple device. These temperature sensitive changes in pixel color correspond to the difference in the amount of heat emitted from open and closed eyelids, as measured by the infrared imager. These temperature changes and corresponding pixel color changes are a result of the increase in emitted heat from the capillary blood flow in the eyelid of the closed eye. This temperature difference is the measurable change that triggers the system to alert the driver. When the eye and facial areas of the driver are in view, the camera provides repeated digitized images of the eyes which is communicated to a video charged couple device with an electronic image array for conversion to an electronic signal.

Baseline normals (eye pixel color and breathing plume temperature) are what is measured immediately upon power connection. An alert driver's open eye color range and exhaled breathing temperatures will be analyzed and sent to the alarm sleep status detector. This memory chip calculates all data derived from the baseline values from each driver after power is connected and then those individuals averages are stored in memory within the video/thermal imager CPU for calculations of baseline normals. Upon a temperature change in baseline memory data below a specified range, the image stabilizer will then zoom the facial area seeking the non-movement associated with drowsiness, then zoom to the eye are for a detection of eye pixel color change from the bluish (cooler) color open eyes baseline data, to a more reddish (warmer) color indicating closed eyes. Associated with each pixel are three colors, typically red, green, and blue, and the video camera determines the intensity parameters of each color component for each pixel. Typically, red represents the most intense heat emitted, and blue indicates the least amount of heat emitted. The digital infrared camera verifies the intensity parameters of each color component for each pixel.

The total change from open eyes to closed eyes is the change that determines sleepiness. A change from sixty percent or greater of the open eye pixel count should be a minimum count to initiate a signal to the microprocessor to evaluate impending change from baseline. The infrared signal pixel color change is the main item that determines eyes are closing and not just the counting of blinks. A steady change in pixel color change is a more accurate method that eliminates falsing.

This double enhancement of monitoring physiological responses to sleep is preferred over all other existing devices which only count eye-blinks or otherwise measure eye closure. It is a further object of the present invention to provide an improved sleep detection and driver alert apparatus that utilizes an digital image stabilization zoom type auto-focusing camera lens to maintain a physically remote means of detecting head movement or lack of movement.

An automatic focus adjusting apparatus for adjusting a focus condition in the objective lens includes a charge couple device (CCD) array for receiving light from an object (facial area including the eyes) and producing an accumulated charge signal representing the opto-electrical signal to be measured. Using the accumulated charge signal that is detected indicates whether or not the heat variations of the object in pixel count is changed from a predetermined level of baseline values.

An alert driver is normally moving their head; looking at traffic, gazing at different things while driving. Whereas, a drowsy driver begins to move the head less and less as they breath in shorter patterns. This shorter pattern brings about a physiological change in the blood carbon dioxide level which increases slightly, called (hypoventilation). This drowsy effect of disorientation coincides with the eye lids beginning to close and sleepiness begins.

In addition, the unit contains an added infrared thermal sensor for measurement of heat variations of the ambient facial area. To monitor temperature variations of said facial area by infrared thermography, the unit will measure the ambient exhaled plume of air associated with normal breathing patterns of an alert driver.

This method comprises the similar steps of observing temperature differentials in the infrared thermal range that occur over the ambient facial surface of nose and mouth. The temperature changes from within the vehicle cabin ambient air (cooler), will be suddenly become higher (warmer) near the nose/mouth with each breath. This pattern is consistent as long as the driver remains alert, conversely a cooler ambient temperature will be present with lower breathing.

The alarm system will be both microchip digitize voice and a buzzer/beep type with progressive loudness. The entire system may be attached to either the dash board or around the rear-view mirror. The device can be either battery operated or plugged into cigarette lighter connection via power cord. The infrared pixel color change is the main essence that determines eyes closing not the counting of blinks. A consistent change in pixel color is more accurate and less likely to false than a method of counting eye blinks in other methods documented.

Using the accumulated number of pixels of the frames recorded by the camera processor, it will then enable the processor to determine the color change from baseline blue to an increasing change to red.

The infrared thermal sensor monitor will be constantly measuring the temperature change in the nose/mouth area to determine ambient values related to baseline data. This will then be process to the data microprocessor for decreases in ambient cooler heat data associated with low breathing.

When measurements of the eye pixel color are found to change approximately 60% or greater from baseline values, and the breathing is lower in temperature by 10%, then the data from both video and thermal circuits are read via the sleep status microprocessor. If baseline values are greater or lesser as described, then the alarm circuit is signaled with its pre-determined beeping and/or voice activation to alert the driver. This double enhancement of monitoring physiological responses to sleep are the preferred embodiment of the invention over all other devices that only count or look at eye blinking or eye closure count alone.

This mode of detection is done by the infrared thermal sensor reading a temperature change within the mouth and nose area of exhaled air. This intensity or change will be sensed by the lower breathing plume that occurs with sleepiness, which is a physiological response to carbon dioxide production. The increase in blood levels of carbon dioxide called respiratory hypoventilation from lower breathing patterns share responsibility for the drowsy/sleepy effect that occurs prior to sleep. The heat change in lower breathing rates that come from the mouth or nose area are the changes that will be measured in the infrared spectrum from ambient facial temperatures with no plume of body temperature gas invading the ambient space.

This sudden change in plume temperature will send information to the microprocessor for a data comparison of the baseline plume temperature at normal tidal breathing patterns of the alert driver.

A warmer temperature would be measured when breathing patterns are normal. A rush of warmer air into the ambient air every 5 seconds from a driver who is alert and oriented would be leaving breathing plumes of exhaled air much higher in temperature; whereas the sleepy/drowsy driver would begin to decrease this breathing pattern with lower more cool exhaled gas plumes. This ambient change in the facial area of nose and mouth would be measurable with close proximity infrared thermal monitoring as described.

This system of the sleep detection thereby eliminates the need for a close proximity device that the driver must wear or have touch the body.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

Detailed Description of the Figures

Figure 1:
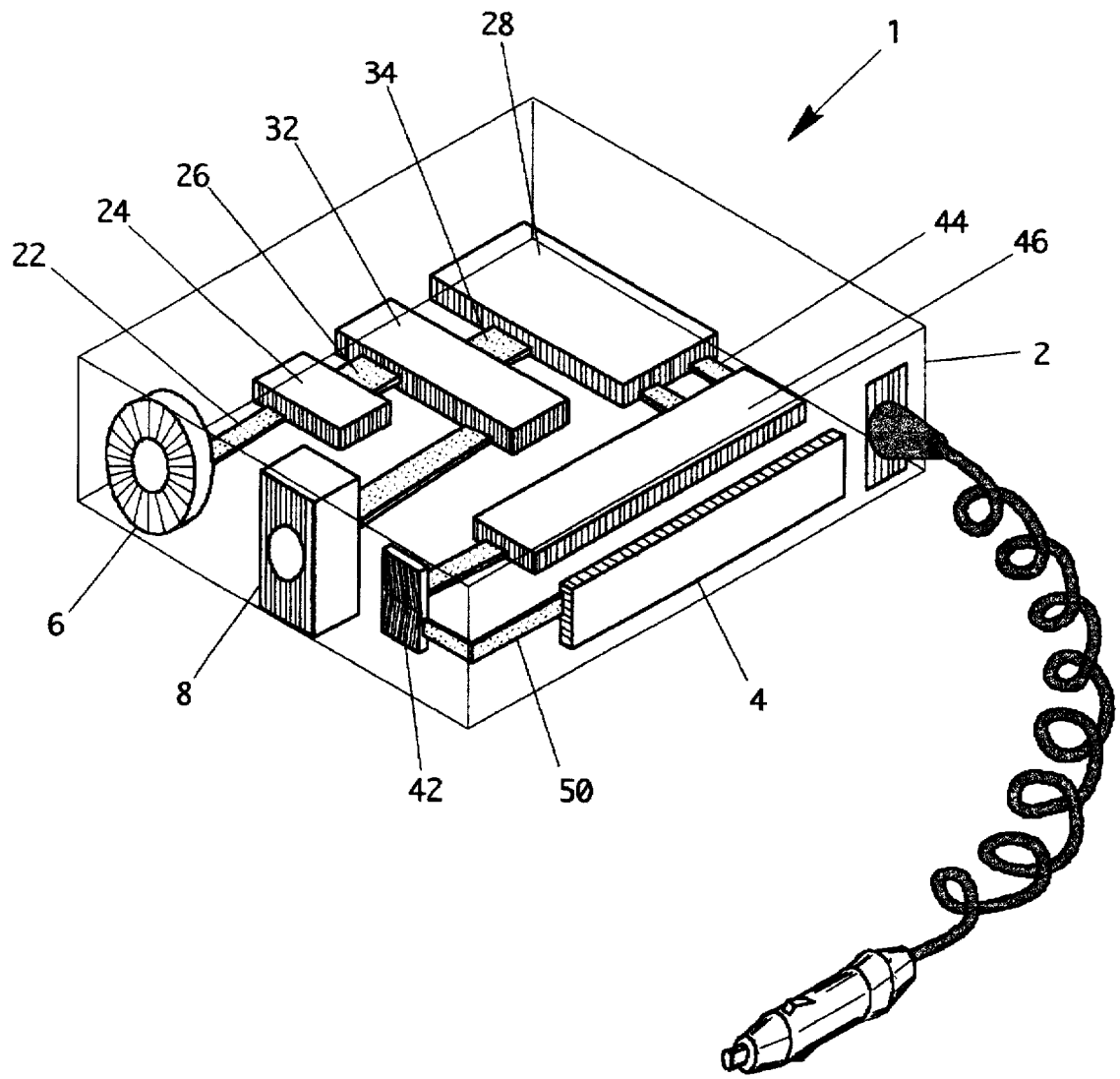
FIG. 1 is an orthographic cutaway view of a sleep detection and driver alert apparatus according to the preferred embodiment of the present invention.
Figure 2:
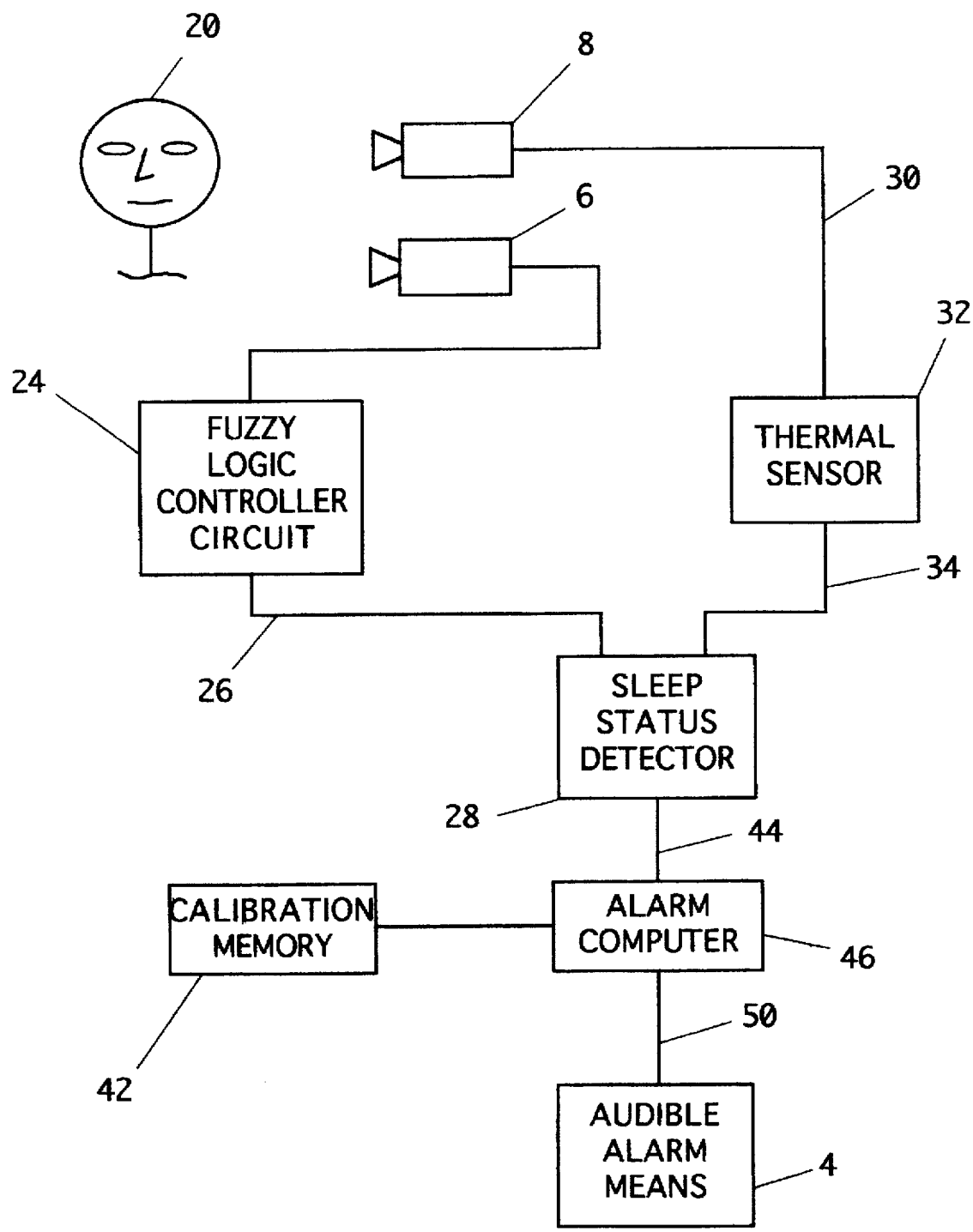
FIG. 2 is a diagrammatical view of the sleep detection and driver alert apparatus depicted in FIG. 1.

Referring now to FIG. 1, a sleep detection and driver alert apparatus 1 is shown, according to the present invention, wherein a housing 2 houses audible alarm means 4, an image stabilization zoom digital auto-focus infrared camera 6, and an infrared thermal sensor 8. Also, and externally access on-off switch 12 is provided Referring to FIG. 2, there is shown the digital infrared auto focus camera 6 located at a distance from the driver's face 20. In its preferred embodiment, the infrared sensor 8 is located the same distance from the driver's face 20. The auto focus infrared zoom camera 6 is transmits the continuously focused image which develops a thermal image pixel color change of the driver's eyes via a first transmission means 22 to a fuzzy logic controller circuit 24. The fuzzy logic controller circuit 24 will transmit a signal via a second transmission means 26 to a sleep status detector 28 upon decrease in head motion below a predetermined limit. Similarly, the infrared thermal sensor 8 transmits the thermal data of the driver's nose and mouth 20 via a third transmission means 30 to a thermal sensor. This thermal ambient temperature is then transmitted via a fourth transmission means 34 to the sleep status detector 28. The sleep status detector 28 then transmits via a fifth transmission means 44 its calculated sleep status information to an alarm computer 46. The alarm computer 46 compares the current information with that in the baseline memory for open eye pixel color count 42, and produces an alarm output 50 to excite the audible alarm means 4 should a sleep state be determined.

Figure 3:
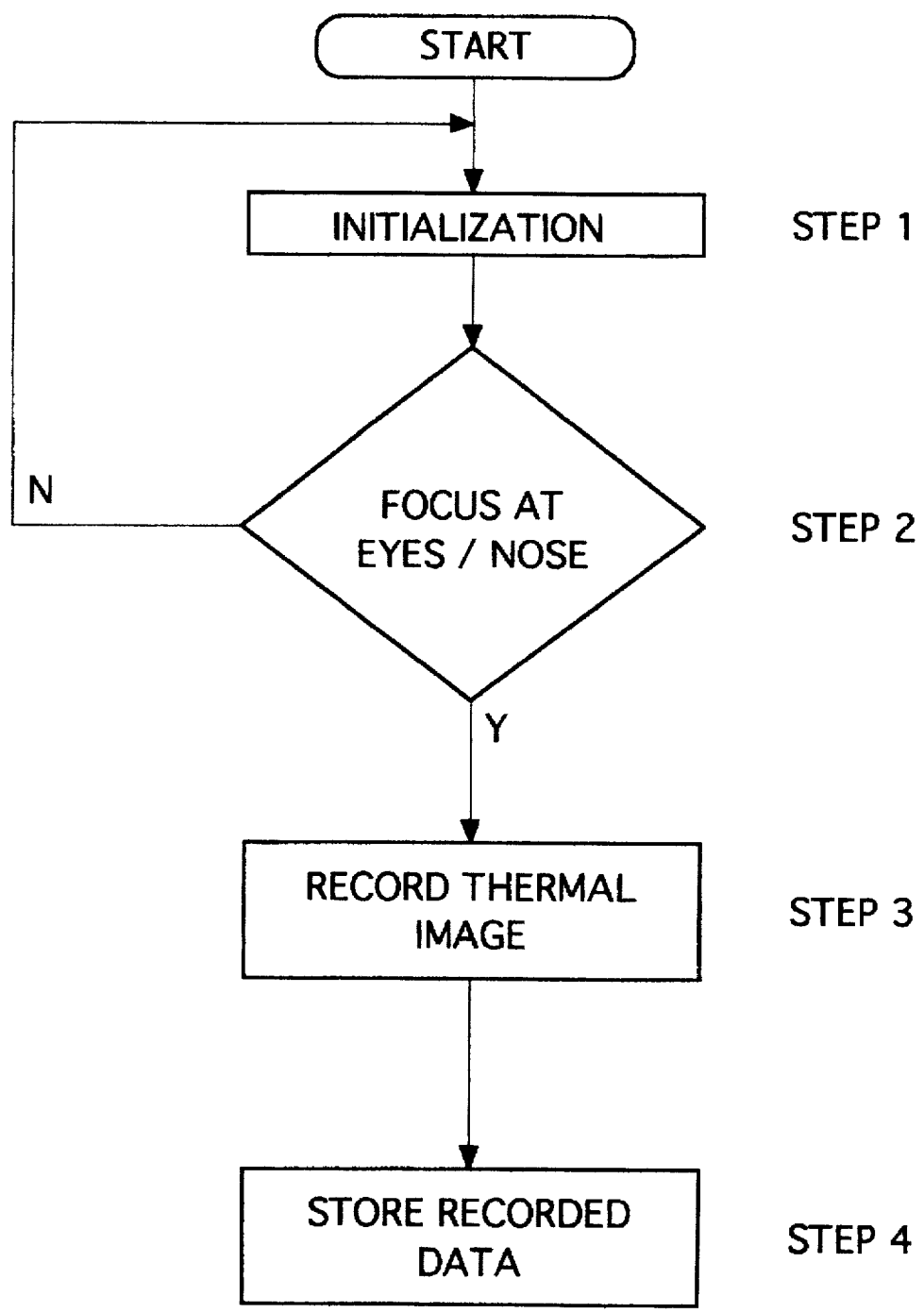
FIG. 3 is a block diagram of the operating logic sequence for calibrating the sleep detection and driver alert apparatus depicted in FIG. 1 and FIG. 2.

FIG. 3 shows the auto calibration logic sequence used for sleep detection and driver alert apparatus 1. The sequence begins with initialization STEP 1, when the apparatus 1 is powered up. Then the auto focus infrared camera 6 takes continuous readings of eye pixel color thermal images, STEP 2. The thermal pixel color image is then recorded in STEP 3. The unit is self calibrating to any driver of different height and distance from the unit.

Figure 4:
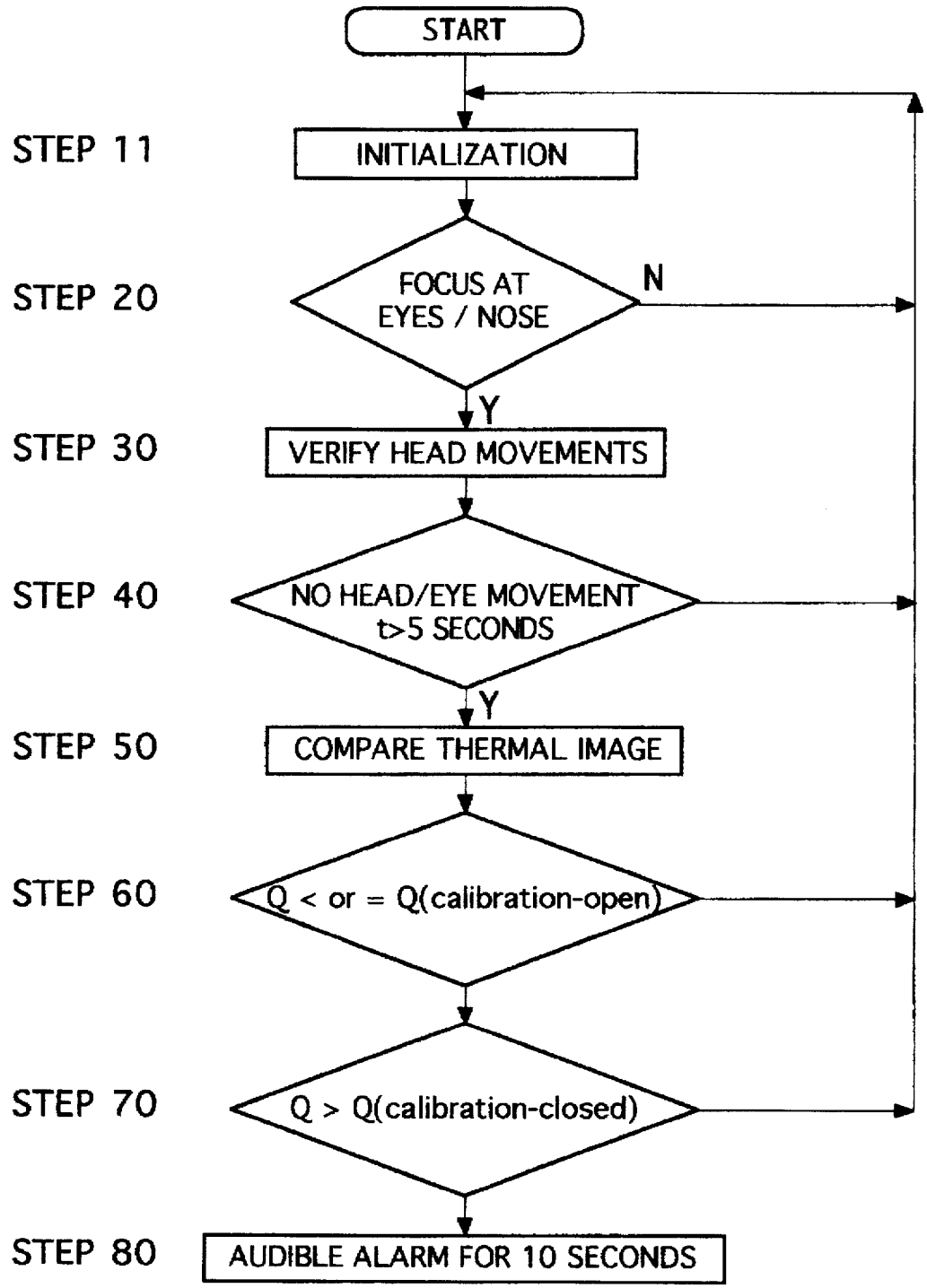
FIG. 4 is a block diagram of the operating logic sequence for the sleep detection and driver alert apparatus depicted in FIG. 1 and FIG. 2.

FIG. 4 in conjunction with FIG. 3 shows the use logic sequence used for sleep detection and driver alert apparatus 1. Initialization begins STEP 11 immediately upon the unit being powered up by the driver. The auto focus camera 6 focuses on the eyes and nose area of the driver continuously, STEP 20. In STEP 30, if head movement is not detected for more than five seconds, the sleep status detector 28 is signaled to analyze the current thermal pixel color image from the calibration memory 42. In STEP 50, the alarm circuit 46 compares the current color pixel count thermal image with the information in the calibration memory 42. In STEP 60, if the thermal pixel count output is determined to be less or greater than that of the calibration data for eyes-open pixel count, then the alarm circuit 46 will further analyze if the thermal signature pixel image is equal to that of the eye's closed data, STEP 70. Finally, if STEP 70 determines that the driver is sleepy by eyelids closing, in STEP 80 an audible alarm is sounded for 10 seconds, in order to wake the sleepy driver. It has been found that a sleepy driver can be determined by a fixed head position with color pixel count change from baseline and low breathing exhaled plume detection.

Operation of the Preferred Embodiment

Figure 5:
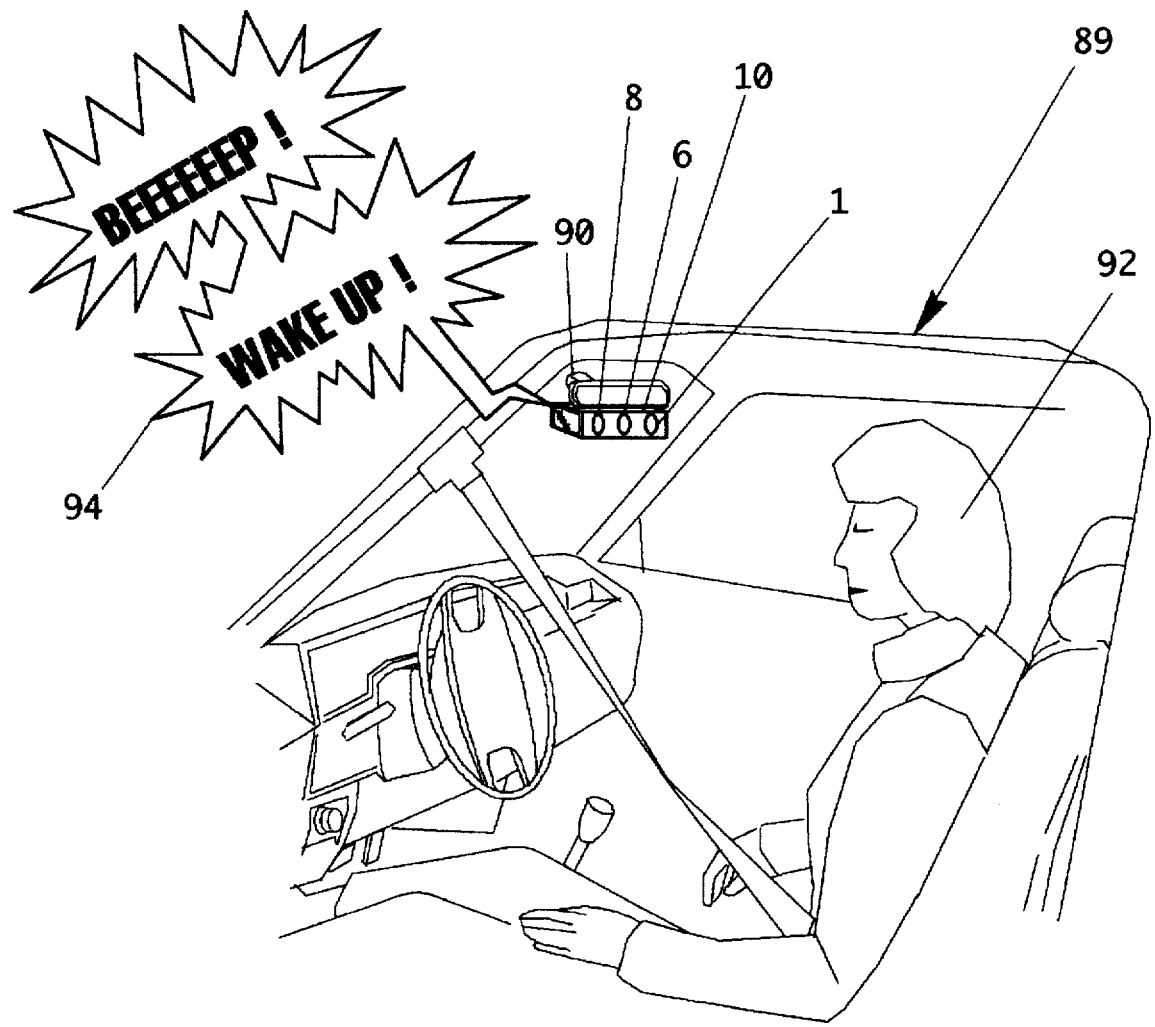
FIG. 5 is an orthographic view of the sleep detection and driver alert apparatus being utilized in an automobile.

In accordance with a preferred embodiment of the present invention, as shown in FIG. 5, the sleep detection and driver alert apparatus 1 is shown in use in an automobile 89 mounted on a rear-view mirror 90. The calibration is automatic.

While operating the vehicle, the sleep detection and driver alert apparatus 1 will continuously focus on the face/eye area to get an accurate image of the driver's eye and head movement. Monitoring the eye and head movement, approximately a five second eye closure would then trigger further detection of heat loss/gain with pixel count as compared with the calibrated auto baseline values. This will prevent false alarms resulting from hand movement, sunlight, or the like. A series of escalating audible alarms 94 are generated to alert or awaken the driver 92.

The foregoing description is included to illustrate the operation of the preferred embodiment and is not meant to limit the scope of the invention. From the foregoing description, many variations will be apparent to those skilled in the art that would yet be encompassed by the spirit and scope of the invention. The scope of the invention is to be limited only by the following claims.

What is claimed is:

1. A sleep detection and driver alert apparatus for sensing sleep or drowsiness in a driver of a motor vehicle or the like, comprising:

a. a containing housing suited to be attached to the rear view mirror or attached to the dashboard of an automobile;

b. an infrared, digital, auto-focus image stabilization zoom camera type lens;

c. thermal sensing means for sensing ambient heat output pixel color changes from a driver's facial mouth and eye area;

d. an optical motion detection circuit for sensing absence of motion from the output of said digital infrared auto-focus image stabilization zoom camera type lens;

e. digital, infrared thermal imaging means for determining changes in infrared thermal output between open and closed eye color pixel changes;

f. sleep status detection means for comparing the output of said optical motion detection circuit, and said thermal sensing means;

g. an auto calibration memory for storing alarm limit and range data for users of differing size, height, and other physical characteristics;

h. an alarm circuit for comparing the output of said sleep status detection means with previously stored calibration information; and i. an audible alarm means for sounding an audible alarm.

2. The sleep detection and driver alert apparatus described in claim 1, wherein said thermal sensing means consists of a means for sensing and measuring thermal output color pixel changes located in the infrared range of the radiation spectrum.

3. The sleep detection and driver alert apparatus described in claim 1, wherein said thermal imaging means consist of an opto-electronic infrared imaging device.

4. The sleep detection and driver alert apparatus described in claim 1, wherein said digital infrared auto-focus image stabilization zoom camera lens has a range in focal length of between one foot and three feet.

5. The sleep detection and driver alert apparatus described in claim 1, wherein said sleep status detection means comprises a microprocessor logic controller.

6. The sleep detection and driver alert apparatus described in claim 1, wherein said alarm means comprises a simulated voice output generated to produce an escalating series of alarms based upon the frequency of the detected sleep episode.

7. A sleep detection apparatus for sensing sleep or drowsiness, comprising:

a. auto focusing sensing means for sensing an individual's face for detecting movement therefrom and generating an image therefrom;

b. an image stabilizer for stabilizing said image generated from said sensing means;

c. thermal imaging means for determining changes in heat output resulting from differences between open and closed eyes via pixel count and changes in lowered respiration rates by means of smaller exhaled plume and temperature variations;

d. an auto-calibration alarm limit and range data for users of differing size, height, and other physical characteristics;

e. an alarm circuit for comparing the output of said sleep status detection means with previously stored calibration information; and f. an audible alarm means for sounding an audible alarm.

8. The sleep detection apparatus described in claim 7, wherein said thermal sensing means consists of a means for sensing and measuring thermal output located in the infrared range of the radiation spectrum for both temperature changes with heat in exhaled breath and pixel color changes in eye area when opened or closed.

9. The sleep detection apparatus described in claim 7, wherein said thermal imaging means consist of an opto-electronic infrared imaging device.

10. The sleep detection apparatus described in claim 7, wherein said sleep status detection means comprises a microprocessor logic controller.

11. The sleep detection apparatus described in claim 7, wherein said audible alarm means comprises a simulated voice output generated to produce an escalating series of alarms based upon the frequency of the detected sleep episodes.

* * * * *